(12) United States Patent
Chen et al.

(10) Patent No.: US 7,016,048 B2
(45) Date of Patent: Mar. 21, 2006

(54) PHASE-RESOLVED FUNCTIONAL OPTICAL COHERENCE TOMOGRAPHY: SIMULTANEOUS IMAGING OF THE STOKES VECTORS, STRUCTURE, BLOOD FLOW VELOCITY, STANDARD DEVIATION AND BIREFRINGENCE IN BIOLOGICAL SAMPLES

(75) Inventors: Zhongping Chen, Irvine, CA (US); J. Stuart Nelson, Laguna Niguel, CA (US)

(73) Assignee: The Regents of the University of California, Oakland, CA (US)

( * ) Notice: Subject to any disclaimer, the term of this patent is extended or adjusted under 35 U.S.C. 154(b) by 312 days.

(21) Appl. No.: 10/410,723

(22) Filed: Apr. 9, 2003

(65) Prior Publication Data

US 2003/0220749 A1 Nov. 27, 2003

Related U.S. Application Data

(60) Provisional application No. 60/371,204, filed on Apr. 9, 2002.

(51) Int. Cl.
*G01B 9/02* (2006.01)

(52) U.S. Cl. ....................................................... 356/497

(58) Field of Classification Search .................. 356/479, 356/477, 497; 250/227.19, 227.27
See application file for complete search history.

(56) References Cited

U.S. PATENT DOCUMENTS

2005/0004453 A1 * 1/2005 Tearney et al. ............. 600/427

* cited by examiner

*Primary Examiner*—Andrew H. Lee
(74) *Attorney, Agent, or Firm*—Daniel L. Dawes; Myers Dawes Andras & Sherman LLP

(57) ABSTRACT

A phase-resolved functional optical coherence tomography system simultaneously obtains the Stokes vectors, structure, blood flow velocity, standard deviation, and birefringence images in human skin. The multifunctional images were obtained by processing the analytical interference fringe signals derived from the two perpendicular polarization detection channels. The blood flow velocity and standard deviation images were obtained by comparing the phase from the pairs of analytical signals in the neighboring A-lines in the same polarization state. The Stokes vectors were obtained by processing the analytical signals from two polarization diversity detection channels for the same reference polarization state. From the four Stokes vectors, the birefringence image, which is insensitive to the orientations of the optical axis in the sample, was obtained. Multifunctional images of a port wine stain birthmark in human skin are demonstrated.

32 Claims, 3 Drawing Sheets

PHASE-RESOLVED FUNCTIONAL OPTICAL COHERENCE TOMOGRAPHY: SIMULTANEOUS IMAGING OF THE STOKES VECTORS, STRUCTURE, BLOOD FLOW VELOCITY, STANDARD DEVIATION AND BIREFRINGENCE IN BIOLOGICAL SAMPLES

RELATED APPLICATIONS

The present application is related to U.S. Provisional Patent Application Ser. No. 60/371,204, filed on Apr. 9, 2002, which is incorporated herein by reference and to which priority is claimed pursuant to 35 USC 119.

GOVERNMENT SUPPORT

This invention was made with Government support under Grant Nos. HL84218, awarded by the National Institutes of Health; Grant No. F49620-00-1-0371, awarded by the Air Force, and Grant No. N00014-94-1-0874 awarded by Office of Naval Research. The Government has certain rights in this invention.

BACKGROUND OF THE INVENTION

1. Field of the Invention

The invention relates to the field of phase-resolved functional optical coherence tomography systems and in particular to systems which can obtain the Stokes vectors, structure, blood flow velocity, standard deviation, and birefringence images in tissue.

2. Description of the Prior Art

Optical coherence tomography (OCT) is a noninvasive, noncontact imaging modality that uses coherent gating to obtain high-resolution cross-sectional images of tissue microstructure. OCT is analogous to ultrasound imaging except that infrared light waves rather than acoustic waves are used. Consequently, the spatial! resolution of OCT is more than an order of magnitude better than that of the ultrasound. OCT was first used clinically in ophthalmology for the imaging and diagnosis of retinal disease. Recently, OCT has been applied to imaging subsurface structure in human skin, blood vessels, oral cavity and the respiratory, urogenital, and GI tracts.

Several extensions of OCT have been developed for functional imaging of tissue physiology. For example, optical Doppler tomography (ODT) combines the Doppler principle with coherence gating for tomographic imaging of tissue microstructure and blood flow simultaneously. See Nelson, et al., "*Method And Apparatus For Optical Doppler Tomographic Imaging Of Fluid Flow Velocity In Highly Scattering Media,*" U.S. Pat. No. 5,991,697 (1999), which is incorporated herein by reference. Polarization sensitive OCT (PS-OCT) combines polarization sensitive detection with OCT to determine tissue birefringence. See De Boer, et al., "*Birefringence Imaging In Biological Tissue Using Polarization Sensitive Optical Coherent Tomography,*" U.S. Pat. No. 6,208,415 (2001), which is incorporated herein by reference. Both techniques use the phase information from the interference fringes to obtain additional physiologically important information. Although a number of potential clinical applications of ODT and PS-OCT have been demonstrated, to date, ODT and PS-OCT imaging have been performed using separate systems. However, there are many clinical indications where determination of both blood perfusion and tissue birefringence is important. For example, in burn injuries both the loss of cutaneous blood perfusion and changes in tissue birefringence are two critical factors used to determine burn depth. Simultaneous imaging of the changes in blood perfusion and collagen birefringence by functional OCT (F-OCT) will according to the invention allow better clinical management of burn injuries.

BRIEF SUMMARY OF THE INVENTION

A phase-resolved functional optical coherence tomography system is disclosed below that can simultaneously obtain the Stokes vectors, structure, blood flow velocity, standard deviation, and birefringence images of human skin. The multifunctional images were obtained by processing the analytical interference fringe signals derived from the two perpendicularly or independently polarized detection channels. The blood flow velocity, and standard deviation images were obtained by comparing the phase from the pairs of analytical signals in the neighboring A-lines in the same polarization state. The Stokes vectors were obtained by processing the analytical signals from two polarization diversity detection channels for the same reference polarization state. From the four Stokes vectors, the birefringence image, which is insensitive to the orientations of the optical axis in the sample, was obtained. Images of structure, flow, standard deviation, phase retardation, and Stokes vectors can be obtained and displayed simultaneously.

The invention is thus defined as an apparatus for phase-resolved functional optical coherence tomography of a sample characterized by optical birefringence comprising an interferometer having a source arm, a reference arm, a sample arm and a detector arm. A source of at least partially coherent polarized light is coupled to the source arm. The partially coherent polarized light is characterized by a well defined polarization state. A polarization modulator is provided, so that polarization modulated light is returned to the detector arm. Polarized light is incident on the sample and arbitrarily polarized light is returned to the detector arm from the sample arm according to sample birefringence. The returned light from the reference arm and sample arm interfere in the detector arm to form polarization interference fringes. A phase modulator is coupled to the interferometer for modulating an optical path length difference between the reference and sample arms of the interferometer at a predetermined phase modulation frequency. A scanner is coupled to the interferometer for scanning the sample. A sensor is coupled to the interferometer for detecting backscattered radiation received by the interferometer from the scanner to detect interference fringes within the interferometer. A polarization demodulator demodulates the polarization interference fringes to generate a complete polarization state description of the backscattered light from the sample by preserving phase relationships between orthogonal components of the polarization interference fringes formed from backscattered light from the sample and from the reference arm. A data processor is coupled to the sensor for processing signals from the sensor corresponding to the interference fringes established by the backscattered radiation in the interferometer and controls the scanner to generate tomographic images. The data processor simultaneously generates the Stokes vectors, and generates tomographic structure, blood flow velocity, standard deviation, and birefringence images at each pixel in the image.

The tomographic images are composed of data from A-line scans of the sample in a given polarization state of the light impinging on the sample. The tomographic blood flow velocity and standard deviation images are generated by the data processor by comparing the phase from pairs of analytical signals in the neighboring A-lines in the same polarization state.

The sensor has two polarization diversity detection channels and the tomographic Stokes vector images are generated by the data processor by processing the analytical signals from the two polarization diversity detection channels for the same reference polarization state. The tomographic birefringence image is generated by the data processor from the four Stokes vectors.

The polarization modulator controls the polarization state of light in the reference arm, which rapidly varies between states orthogonal in the Poincare sphere at a predetermined frequency to insure that birefringence measurements are independent of orientations of the optical axis of the sample. The sensor detects four states of light polarization at each pixel. The data processor controls the scanner to sequentially perform a predetermined number of lateral line scans, A-line scans, for each polarization state. The data processor generates Doppler frequency shift ($f_n$) and standard deviation $\sigma_n$ values at the nth pixel with complex analytical signals from the four sequential A-scans. The data processor generates an average of the Doppler frequency shift ($f_n$) and standard deviation $\sigma_n$ values at the nth pixel for each polarization state to generate tomographic Doppler shift and variance images.

The sensor detects two orthogonal polarization diversity channels, and the data processor generates the coherence matrix therefrom to generate the Stokes vectors characterizing the polarization state of the backscattered light, and the light intensity. The data processor generates the Stokes vectors according to:

$$S_{0,n} = \sum_{m=n-M/2}^{n+M/2} \sum_{j=1}^{4} \left[ \tilde{\Gamma}_j^H(t_m)\tilde{\Gamma}_j^{H*}(t_m) + \tilde{\Gamma}_j^V(t_m)\tilde{\Gamma}_j^{V*}(t_m) \right]$$

$$S_{1,n} = \sum_{m=n-M/2}^{n+M/2} \sum_{j=1}^{4} \left[ \tilde{\Gamma}_j^H(t_m)\tilde{\Gamma}_j^{H*}(t_m) - \tilde{\Gamma}_j^V(t_m)\tilde{\Gamma}_j^{V*}(t_m) \right]$$

$$S_{2,n} = \sum_{m=n-M/2}^{n+M/2} \sum_{j=1}^{4} 2\mathrm{Re}\left[ \tilde{\Gamma}_j^{H*}(t_m)\tilde{\Gamma}_j^V(t_m) \right]$$

$$S_{3,n} = \sum_{m=n-M/2}^{n+M/2} \sum_{j=1}^{4} 2\mathrm{Im}\left[ \tilde{\Gamma}_j^{H*}(t_m) \right]$$

where $\Gamma_j^H(t_m)$ and $\Gamma_j^V(t_m)$ are the complex signals detected from the two orthogonal polarization channels at axial rime $t_m$ for the jth A-scan, $\Gamma_j^{H*}(t_m)$ and $\Gamma_j^{V*}(t_m)$ are their conjugates. The data processor generates the structural image from averaging the Stokes vectors for the four states of light polarization. The data processor generates the phase retardation image from $S_0$, which characterizes the birefringence distribution in the sample by the rotation of the Stokes vectors in the Poincare sphere.

The invention further includes a method performed by the above combination of elements. In particular the invention includes a method of performing phase-resolved F-OCT to simultaneous image the Stokes vectors, structural, Doppler frequency shift, standard deviation, and birefringence of a sample comprising the steps of scanning the sample; performing PS-OCT while scanning each pixel location; simultaneously performing ODT while scanning each pixel location; determining the Stokes vectors at each pixel location; and generating the tomographic structural, Doppler frequency shift, standard deviation, and birefringence images of the sample.

The method further comprising the step of averaging in the generation of the Doppler frequency shift and standard deviation to reduce the influence of speckle noise and tissue birefringence artifacts.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

In the illustrated embodiment, we describe a phase-resolved F-OCT system that can simultaneously obtain the Stokes vectors, structure, blood flow velocity, standard deviation, and birefringence images in human skin or tissue. The system is based on a phase-resolved signal processing method whereby the multifunctional images were obtained by processing the analytical interference fringe signals derived from two perpendicular polarization detection channels.

Figure 1:
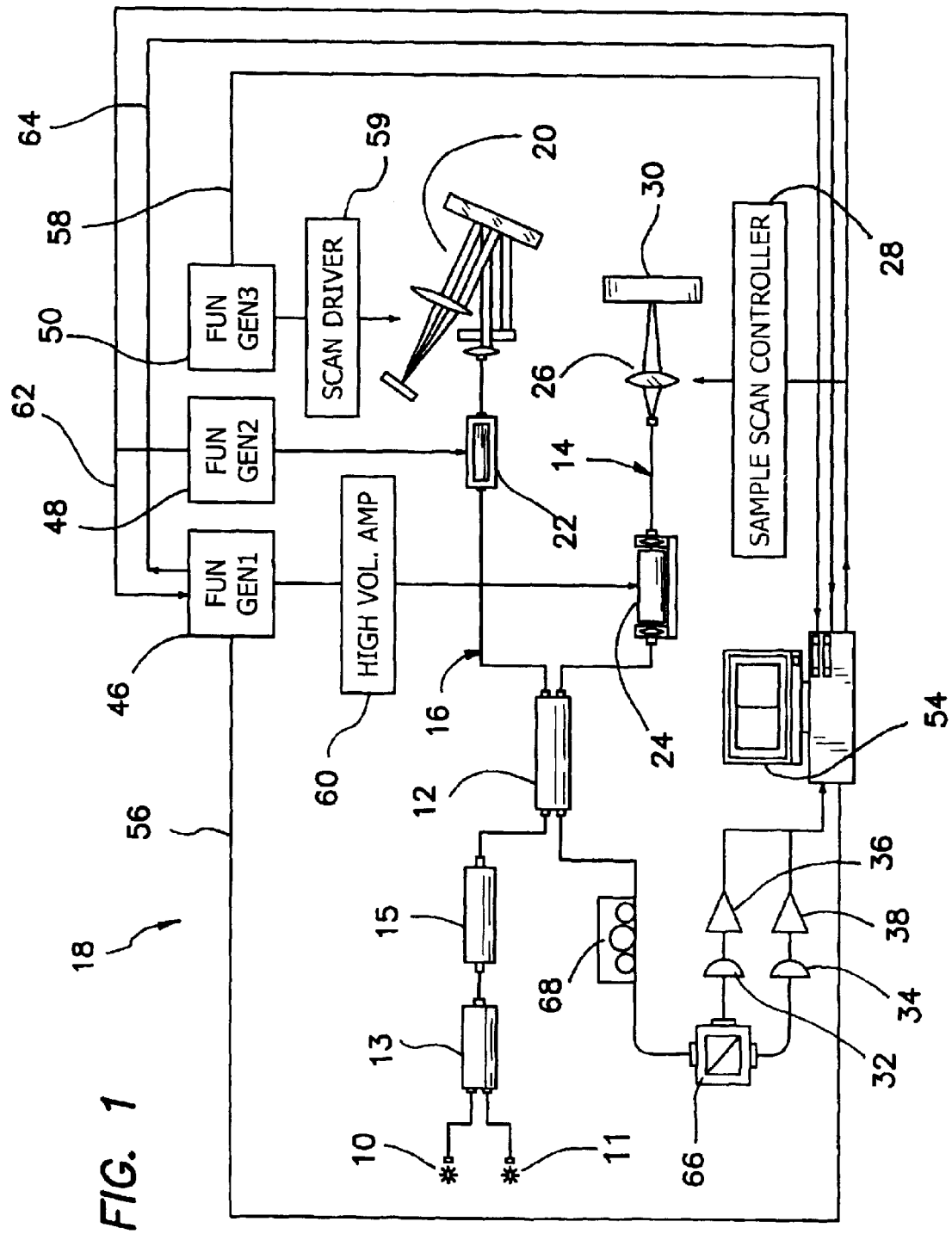
FIG. 1 is a simplified block diagram of the F-OCT system of the invention.

The fiber-based high-speed F-OCT system for multifunctional imaging is shown in the diagrammatic depiction of FIG. 1. A 1300 nm partially coherent broadband light source 10 manufactured by AFC Technologies with a full-width-half-maximum (FWHM) bandwidth of 80 nm was used as the light source. A visible light source, such as a semiconductor laser 11 is used as an aiming source, but otherwise plays no significant role in the data imaging. Source 10 and laser 11 are combined by means of a 2×1 coupler 13 and provided as input to a polarizer 15. In the illustrated embodiment polarizer 15 linearly polarizes the light provided to a 2×2 fiber splitter 12. Light entering splitter 12 is divided between a sample arm 14 and a reference arm 16 of the Michelson interferometer, generally denoted by reference numeral 18.

In the reference arm 16 a rapid scanning optical delay (RSOD) line 20 is aligned such that only group delay scanning at 500 Hz is generated without phase modulation. RSOD line 20 is conventional and is generally described in Tearney et. al., Opt. Lett. 22, 1811 (1997) and Rollins et.al., Optics Express 3, 219 (1998). A stable phase modulation at 500 kHz is generated using an E-O modulator 22 for heterodyne detection. Phase modulator 22 in reference arm 16 is driven by function generator 48, which in turn is controlled by a general purpose interface bus 56 (GPIB) from a data acquisition (DAQ) board in computer 54. Function generator 48 generates a TRIGGER OUT signal communicated on line 64 to computer 54 for arming the DAQ board. The galvanometer in RSOD 20 is similarly driven by a scan driver generator 59 coupled to function generator 50 which in turn is coupled to bus 56 and generates a synchronization signal, SYN OUT, which is provided on line 58 to computer 54 for driving the galvanometer scanner in RSOD 20. Polarization modulator 24 in sample arm 14 is driven by high voltage amplifier 60, which in turn is controlled by function generator 46 coupled to bus 56 and TRIGGER IN signal communicated from computer 54 on line 62.

A probe 26 with a collimator and infinity-corrected objective driven by a translation stage or stage controller 28 is employed in the sample arm 14 to scan sample 30. Stage controller 28 is coupled to line 62, TRIGGER IN. The backscattered light is transmitted through polarization modulator 24 through coupler 12 to polarization control 68 to polarization beam splitter 66. Polarization control 68 is a mechanically adjustable fiber loop polarizer, which serves to equalize the amount of light in each of two orthogonal polarization states sent to polarization beam splitter 66, which has been received in the detector arm from reference arm 16. The backscattered light signal or fringe signals from the two polarization channels are separated by polarization beam splitter 66 and detected by two photo-detectors 334 and 32, then high pass filtered, amplified and digitized by a 12-bit, analogue-to-digital conversion board 36/38 (dual-channel, 5M samples per channel, National Instruments).

Polarization modulator 24 is used to control the polarization state of light in the sample arm 14, which rapidly varied between states orthogonal in the Poincare sphere at 125 Hz. In the illustrated embodiment, polarization modulator 24 is driven to provide in sequence four linearly independent polarization states corresponding to the four Stokes vectors. For example, the four linearly independent polarization states may be vertically and horizontally linearly polarized light and clockwise and counterclockwise circularly polarized light, or any other four linearly independent polarization states as may be desired. The choice of orthogonal polarization states in the Poincare sphere is important because it insures the birefringence measurements will be independent of orientations of the optical axis in the sample 30. In order to measure the Stokes vectors accurately, four states of light polarization are generated for each lateral location. For each polarization state, four A-line scans are performed sequentially. Therefore, a total of 16 A-line scans are used to calculate the Stokes vectors, phase retardation, structure, Doppler mean frequency, and Doppler standard deviation images simultaneously.

Also, if polarization modulator 24 is controlled to provide the four Stokes vectors, the Mueller matrix of sample 30 may be measured. For example, $$\begin{pmatrix} S'_0 \\ S'_1 \\ S'_2 \\ S'_3 \end{pmatrix} = \begin{pmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{pmatrix} \begin{pmatrix} S_0 \\ S_1 \\ S_2 \\ S_3 \end{pmatrix}$$

where $$\begin{pmatrix} S'_0 \\ S'_1 \\ S'_2 \\ S'_3 \end{pmatrix}$$

is the Stokes vector after reflection from sample 30, $$\begin{pmatrix} S_0 \\ S_1 \\ S_2 \\ S_3 \end{pmatrix}$$

is the Stokes vector incident on sample 30 and $$\begin{pmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{pmatrix}$$

is the Mueller matrix. By providing through control of polarization modulator 24 light having the pure Stokes vectors $S_0$, $S_1$, $S_2$ and $S_3$ incident on sample 30, the elements of the Mueller matrix, can be readily derived in computer 54, i.e. for $$S = S_0 = \begin{pmatrix} 1 \\ 0 \\ 0 \\ 0 \end{pmatrix},$$

then $$S' = \begin{pmatrix} M_{11} \\ M_{21} \\ M_{31} \\ M_{41} \end{pmatrix}$$

and similarly for each of the other Stokes vectors $S_1$, $S_2$ and $S_3$.

Figure 2:
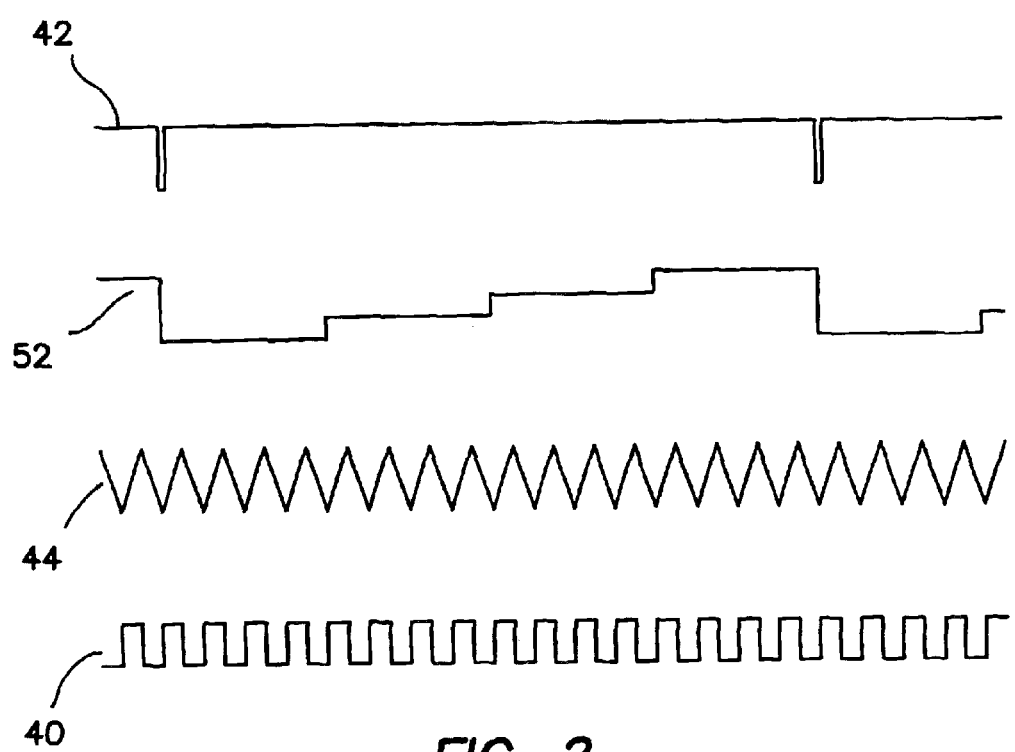
FIG. 2 is a synchronizing time clock diagram for the system of FIG. 1.

The synchronizing time clock diagram is shown in FIG. 2. Channel 1 on line 42 is the signal generated nom the synchronized TRIGGER OUT from function generator 46, and it arms the A-to-D conversion in computer 54. Channel 2 on line 52 is the signal generated by function generator 48 to control the polarization modulator 24. Channel 3 on line 44 is the triangle signal from the function generator 50 to control the galvanometer scanning. Channel 4 on line 40 is the signal generated by SYN OUT of function generator 50 through a digital delay. This signal is used to trigger the phase modulation and data acquisition.

The positive slope of the signal shown on line 40 acts as a trigger to start the phase modulation signal generation and data acquisition. The negative slope acts as a trigger to stop the phase modulation signal generation and data acquisition. The negative slope of this signal triggers the start of polarization modulation signal generation. The data acquisition (DAQ) is ready for the four states of light polarization when the TRIGGER OUT signal in line 42 has a negative slope. Line 44 is the triangle signal driving the galvanometer scanner which is RSOD 20. The driving signals for the polarization state modulator 24, phase modulator 22 and galvanometer scanner in the RSOD 20 are all generated from bus signals by the three function generators 46, 48 and 50. The translation stage 28 is controlled by bus 56 so that it moves one pixel when the signal in line 52 of FIG. 2 has run four steps.

Because Doppler and polarization sensitive detection requires phase information, we first calculate the complex analytical signal Γ(t) of the interference fringe using Hilbert transform $$\tilde{\Gamma}(t) = \Gamma(t) + \frac{i}{\pi} P \int_{-\infty}^{\infty} \frac{\Gamma(t')}{t'-t} dt' \quad (1)$$

Where P denotes the Cauchy principle value. Because the interference signal Γ(t) is quasi-monochromatic, the complex analytical signal is given by:

$$\tilde{\Gamma}(t) = 2 \int_0^{\infty} \int_{-T}^{T} \Gamma(t') \exp(-2\pi i v t') dt' \exp(2\pi i v t) dv \quad (2)$$

The digital approach to determine the complex analytical signal using Hilbert transformation is shown in the following block diagram Γ(t)→FFT→×H(v)→band pass filter→FFT$^{-1}$→$\tilde{\Gamma}$(t)

where FFT denotes the fast Fourier transform, x is a multiplying symbol and H(v) is the Heaviside function given by:

$$H(v) = \begin{cases} 0 & v < 0 \\ 1 & v \geq 0 \end{cases} \quad (3)$$

and FFT$^{-1}$ denotes the inverse fast Fourier transform. Multiplication of the Heaviside function is equivalent to performing an operation that discards the spectrum in the negative frequency region.

For each polarization state, four sequential A-scans are performed. The Doppler frequency shift ($f_n$) and standard deviation $\sigma_n$ values at the nth pixel can be calculated with complex analytical signals from the four sequential A-scans:

$$f_n = \frac{1}{2\pi T} \tan^{-1}\left( \frac{\text{Im}\left( \sum_{m=n-M/2}^{n+M/2} \sum_{j=1}^{3} \tilde{\Gamma}_j(t_m) \tilde{\Gamma}^*_{j+1}(t_m) \right)}{\text{Re}\left( \sum_{m=n-M/2}^{n+M/2} \sum_{j=1}^{3} \tilde{\Gamma}_j(t_m) \tilde{\Gamma}^*_{j+1}(t_m) \right)} \right) \quad (4)$$

$$\sigma^2 = \frac{1}{2\pi^2 T^2} \left( 1 - \frac{\left| \sum_{m=n-M/2}^{n+M/2} \sum_{j=1}^{3} \tilde{\Gamma}_j(t_m) \tilde{\Gamma}^*_{j+1}(t_m) \right|}{\frac{1}{2} \left( \sum_{m=n-M/2}^{n+M/2} \sum_{j=1}^{3} [\tilde{\Gamma}_j(t_m) \tilde{\Gamma}^*_j(t_m) + \tilde{\Gamma}_{j+1}(t_m) \tilde{\Gamma}^*_{j+1}(t_m)] \right)} \right) \quad (5)$$

where $\Gamma_j(t_m)$ and $\Gamma^*_j(t_m)$ are the complex signals at axial time $t_m$ corresponding to the jth A-scan and its conjugate respectively, $\Gamma_{j+1}(t_m)$ and $\Gamma^*_{j+1}(t_m)$ are the complex signals at axial time $t_m$ corresponding to the next A-scan and its conjugate, respectively, T is the time duration between A-scans, and M is an even number that denotes the window size in the axial direction for each pixel. This algorithm also effectively reduces speckle noise. The calculated Doppler frequency shifts and standard deviation values from each polarization state is then averaged to obtain Doppler shift and variance images.

For every polarization state controlled by the polarization modulator 24, the A-scan signals corresponding to the two orthogonal polarization diversity channels were digitized. Considering the quasi-monochromatic light beam, the coherence matrix can be calculated from the complex electrical field vector from these two channels:

$$J = \begin{pmatrix} \langle E^*_H(t) E_H(t) \rangle & \langle E^*_H(t) E_V(t) \rangle \\ \langle E^*_V(t) E_H(t) \rangle & \langle E^*_V(t) E_V(t) \rangle \end{pmatrix} = \begin{pmatrix} J_{HH} & J_{HV} \\ J_{VH} & J_{VV} \end{pmatrix} \quad (6)$$

where $E_H$, and $E_V$ are the components of the complex electric field vector corresponding to the horizontal and vertical polarization channels, respectively, and $E^*_H$, and $E^*_V$ are their conjugates, respectively. The Stokes vector can be derived from the coherence matrix:

$$S_0 = J_{HH} + J_{VV}$$

$$S_1 = J_{HH} - J_{VV}$$

$$S_2 = J_{HV} + J_{VH}$$

$$S_3 = i(J_{VH} - J_{HV}) \quad (7)$$

where $S_0$, $S_1$, $S_2$, and $S_3$ are the four components of the Stokes vector. $S_1$, $S_2$, and $S_3$ are the coordinates of the Stokes vector in the Poincare sphere characterizing the polarization state of the backscattered light, and $S_0$ is the module of the Stokes vector characterizing light intensity. The Stokes vector for the nth pixel and one state of light polarization can be calculated as:

$$S_{0,n} = \sum_{m=n-M/2}^{n+M/2} \sum_{j=1}^{4} [\tilde{\Gamma}_j^H(t_m) \tilde{\Gamma}_j^{H*}(t_m) + \tilde{\Gamma}_j^V(t_m) \tilde{\Gamma}_j^{V*}(t_m)]$$

$$S_{1,n} = \sum_{m=n-M/2}^{n+M/2} \sum_{j=1}^{4} [\tilde{\Gamma}_j^H(t_m) \tilde{\Gamma}_j^{H*}(t_m) - \tilde{\Gamma}_j^V(t_m) \tilde{\Gamma}_j^{V*}(t_m)]$$

$$S_{2,n} = \sum_{m=n-M/2}^{n+M/2} \sum_{j=1}^{4} 2\text{Re}[\tilde{\Gamma}_j^{H*}(t_m) \tilde{\Gamma}_j^V(t_m)]$$

$$S_{3,n} = \sum_{m=n-M/2}^{n+M/2} \sum_{j=1}^{4} 2\text{Im}[\tilde{\Gamma}_j^{H*}(t_m)] \quad (8)$$

where $\Gamma_j^H(t_m)$ and $\Gamma^V_j(t_m)$ are the complex signals detected from the two orthogonal polarization channels at axial rime $t_m$ for the jth A-scan, $\Gamma_j^{H*}(t_m)$ and $\Gamma^{V*}_j(t_m)$ are their conjugates. From the Stokes vectors for the four states of light polarization the structural image is obtained by averaging the four. $S_0$, the phase retardation image, which characterizes the birefringence distribution in the sample, is calculated by the rotation of the Stokes vectors in the Poincare sphere.

Figure 3:
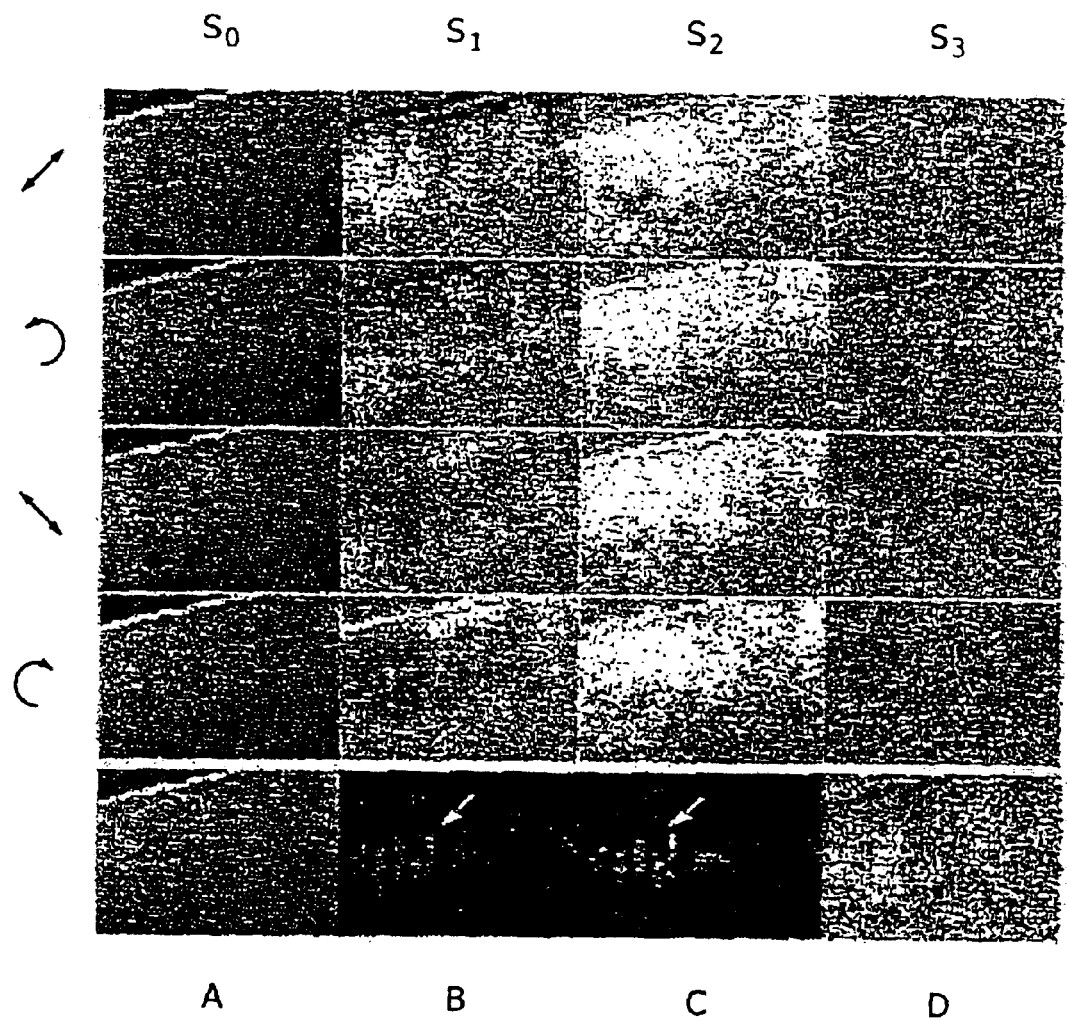
FIG. 3 is an example of the data output of the system of FIG. 1 showing the simultaneous imaging of the Stokes vectors, structure, blood flow velocity, standard deviation and birefringence information from in vivo human skin. The top four panels are the Stokes vector images corresponding to the four reference polarization states. The bottom four panel images are: A: structural image; B: blood flow velocity image; C: standard deviation image; and D: phase retardation image.

We have used our phase-resolved F-OCT system to perform in vivo imaging of a port wine stain birthmark in human skin. The simultaneous imaging of the Stokes vectors, structure, blood flow, velocity, standard deviation, and birefringence is shown in the collection of data images which comprise FIG. 3. The image area is 2 mm×1.5 mm. The top four, columnar panels are the Stokes vectors corresponding to the four different, polarization states shown in FIG. 2. From left to right, they are $S_0$, $S_1$, $S_2$, and $S_3$, respectively, obtained by averaging four A-lines in every polarization state. The bottom row of images are structure, Doppler frequency shift (blood flow velocity), standard deviation, and birefringence images. Implementation of the polarization diversity detection in the intensity, Doppler and standard deviation images significantly reduces the artifact due to tissue birefringence. In addition, speckle noise is also greatly reduced. The greater detail noted in the structure image as compared to the So image indicates that the speckle noise is greatly reduced when polarization diversity detection is used. Small vessels can be clearly identified in the Doppler frequency shift and standard deviation images. The arrows in the Doppler frequency shift and standard deviation images indicate that the blood vessels are located approximately 500 µm below the skin surface. The nonuniform birefringence of human skin can also be identified in the phase retardation image.

In summary, we have developed a phase-resolved F-OCT system capable of simultaneous imaging of the Stokes vectors, structure, Doppler frequency shift, standard deviation, and birefringence by combining PS-OCT and ODT. The detection scheme we implemented in our F-OCT system allows polarization diversity averaging in the detection of the Doppler frequency shift and standard deviation, which greatly reduces the influence of speckle noise and tissue birefringence artifacts. Given the noninvasive nature and exceptional high spatial resolution, phase-resolved F-OCT that can simultaneously provide tissue structure, blood perfusion, and birefringence information has great potential for both basic biomedical research and clinical medicine.

While it is recognized that optical coherence tomography (OCT) is a non-invasive technique that images tissue structure up to a depth of 2 mm with spatial resolution of 10 µm. We have extended the capability of OCT with optical Doppler tomography (ODT), which measures depth resolved flow in tissue, and polarization sensitive OCT (PS-OCT), which measures depth resolved polarization changes of reflected light.

These three imaging modalities give functional information, namely structure, flow and polarization, in biological tissues and have a wide range of applications in medicine, which include: determination of burn depth; guidance regarding the optimal depth for burn debridement prior to definitive closure; imaging and diagnosis of corneal and retinal pathology; diagnosis and treatment of tumors in the gastrointestinal and respiratory tracts, cervix, and skin; monitoring of tissue perfusion and viability immediately after injury, wound closure, replantation, or microvascular reconstruction; optimized radiation dosimetry by assessing and quantifying alterations in tissue microvascular and matrix structure; determination of long-term alterations in microvascular hemodynamics and morphology in chronic diseases such as diabetes mellitus and arteriosclerosis; and mapping of conical hemodynamics with high spatial resolution for brain research.

The critical challenge in burn treatment is to assess the depth of the thermal injury accurately in order to determine whether the burn can heal spontaneously or whether surgical intervention is required; because of the thin and complex nature of human skin, burn depth variations on the order of 100 µm can make the difference between spontaneous epithelial regeneration or surgical intervention with skin grafting. This decision is particularly crucial on cosmetically and functionally important areas such as the face and hands where the skin is 1-2 mm thick.

There are two critical factors in burn depth determination due to thermal damage: (1) loss of cutaneous blood circulation, and (2) changes in tissue structure. Tissue perfusion introduces a Doppler shift on reflected light. Experiments with fluorescein fluorometry and laser Doppler flowmetry (LDF) have demonstrated that the cutaneous microcirculation plays a crucial role in determining whether a burn can heal spontaneously through epithelial regeneration. The birefringence of collagen in human skin changes the polarization state of light. Thermal denaturation, which occurs between 56–65° C. reduces birefringence by changing the collagen from a rod-like to a random coil structure. PS-OCT/ODT measures spatially resolved changes in the polarization state and Doppler shift of light reflected from human skin up to a depth of 1–2 mm with 10–30 µm resolution. Changes in blood perfusion and collagen birefringence due to thermal denaturation can be used for burn depth determination in human skin.

Information provided by PS-OCT/ODT can be important during all stages of burn wound management. Preoperatively, the burn surgeon can decide on one of two possible treatment plans for casualties with burn injuries: (a) concentrate on supporting the patient while the burn wound evolves and wound healing begins; or (b) immediate burn debridement with skin grafting. Intraoperatively, PS-OCT/ODT provides guidance regarding the optimal depth for burn debridement prior to definitive closure. Postoperatively, PS-OCT/ODT can be used to monitor physiologically significant healing events including neovascularization. The potential to rapidly and accurately image and distinguish viable from nonviable tissue over large areas and at different depths is of enormous benefit to the attending burn surgeon.

Ocular blood flow and retinal nerve fiber layer thickness determination is also an area of application of the invention. Ocular disease can have a devastating impact on a patient's quality of life. Because the uninterrupted optical pathway allows direct visual observation of nervous and vascular tissue, the eye provides an important indicator of not only ophthalmologic but also systemic vascular and neurologic disease. Much ocular pathology involves disturbances in blood flow, including diabetic retinopathy, low tension glaucoma, anterior ischemic optic neuritis, and macular degeneration. For example, in diabetic retinopathy, retinal blood flow is reduced and the normal autoregulatory capacity deficient. Ocular hemodynamics are altered in patients with glaucoma and severe loss of visual function has been associated with reduced macular blood flow.

Polarization and Doppler shift sensitive depth-resolved measurements of light reflected from the retina can be used to determine the retinal nerve fiber layer (NFL) thickness and retinal perfusion with high sensitivity and spatial resolution simultaneously.

In summary, the range of applications of the invention includes:

Cancer diagnosis in the gastrointestinal (GI), respiratory, and urogenital tracts (including larynx, bladder, uterine_cervix etc.).

Cancer/diagnosis in skin

Diagnosis of cardiovascular disease

Generation of an in situ three-dimensional tomographic image and velocity profiles of blood-perfusion in human skin at discrete spatial locations in either the superficial or deep dermis;

Burn depth determination; provide guidance regarding the optimal depth for burn debridement prior to definitive closure;

Determination of tissue perfusion and viability immediately after injury, wound closure, replantation, or transposition of either rotational or free skin flaps;

Evaluation of the vascular status of a buried muscle flap covered by a split thickness skin graft; perfusion in the superficial and deeper flap components can be monitored separately;

Distinguishing between arterial or venous occlusion and determine the presence and/or extent of adjacent post-traumatic arterial or venous vascular injury by providing an situ tomographic image and velocity profile of blood flow;

Monitoring the effects of pharmacological intervention on skin microcirculation (e.g., effects of vasoactive compounds or inflammatory mediators; determination of transcutaneous drug penetration kinetics; evaluation of the potency of penetration enhancers; irritation of chemical compounds, patch-test allergens and ultraviolet radiation; comparison of the reactivity of the skin microcirculation in different age and ethnic groups);

Determination of the extent of intestinal vascular insufficiency or infarction; to conserve intestine by confining resection to nonvascularized segments;

Measurement of ocular, blood flow and birefringence, diagnosis of ocular disease;

Imaging of three-dimensional tumor microvasculature for angiogenesis research;

Optimizing radiation dosimetry by assessing and quantifying alterations in tissue microvascular and matrix structure;

Determining long-term alterations in microvascular hemodynamics and morphology in chronic diseases such as diabetes mellitus and arteriosclerosis;

Mapping cortical hemodynamics with high spatial resolution for brain research;

Guiding surgical procedures for brain surgery

Finally, phase resolved F-OCT with axicon lens is also attractive for the following industrial applications:

Imaging flow dynamics in microchannels of micro-electro-mechanic system (MEMS) chips.

Characterizing and monitoring of flow velocity when the fluid is encapsulated in highly scattering materials such as fibrous substances or resin composites;

Accurately measuring particle concentration and size, and fluid flow velocity profile and providing useful diagnostic information for process monitoring and quality control;

Monitoring in situations involving turbid fluid flow samples such as materials processing of paints, pigmented fluids, and other types of opaque liquids; and Characterizing and monitoring of dry particulate flow within conduits such as a jet stream; here, a significant advantage of DOT is that the flow could be characterized and "monitored without disturbing the stream.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for phase-resolved functional optical coherence tomography of a sample characterized by optical birefringence comprising:

an interferometer having a source arm, a reference arm, a sample arm and a detector arm;

a source of at least partially coherent polarized light coupled to the source arm, the partially coherent polarized light being characterized by a well defined polarization state;

a polarization modulator for providing modulated polarized light of selected linearly independent polarization states incident on the sample, wherein backscattered arbitrarily polarized modulated light is returned to the detector arm from the sample arm according to sample birefringence, the returned light from the reference arm and sample arm interfering in the detector arm to form polarization interference fringes;

a phase modulator coupled to the interferometer for modulating an optical path length difference in the reference and sample arms of the interferometer at a predetermined phase modulation frequency;

a scanner coupled to the interferometer for scanning the sample;

a sensor coupled to the interferometer for detecting backscattered radiation received by the interferometer from the scanner to detect interference fringes within the interferometer; and a polarization demodulator to demodulate the polarization interference fringes; and a data processor coupled to the sensor for processing signals from the sensor corresponding to the interference fringes established by the backscattered radiation in the interferometer and for controlling the scanner to generate tomographic images to generate a complete polarization state description of the backscattered light from the sample by preserving phase relationships between orthogonal components of the polarization interference fringes formed from backscattered light from the sample and from the reference arm, and wherein the data processor simultaneously generates the Stokes vectors, and generates tomographic structure, blood flow velocity, standard deviation, and birefringence images at each pixel in the image.

2. The apparatus of claim 1 where the tomographic images are composed of data from A-line scans of the sample in each of the polarization states of the light impinging on the sample, and where the tomographic blood flow velocity and standard deviation images are generated by the data processor by comparing the phase from pairs of analytical signals in the neighboring A-lines in the same polarization state.

3. The apparatus of claim 1 where the sensor has two polarization diversity detection channels and where the tomographic Stokes vector images are generated by the data processor by processing the analytical signals from the two polarization diversity detection channels for the same reference polarization state.

4. The apparatus of claim 3 where the tomographic birefringence image is generated by the data processor from the four Stokes vectors.

5. The apparatus of claim 1 where the polarization modulator controls the polarization state of light in the sample arm, which rapidly varies between states orthogonal in the Poincare sphere at a predetermined frequency to insure that birefringence measurements are independent of orientations of the optical axis of the sample.

6. The apparatus of claim 1 where the sensor detects four polarization states of light at each pixel.

7. The apparatus of claim 6 where the data processor controls the scanner to sequentially perform a predetermined number of lateral line scans, A-line scans, for each polarization state.

8. The apparatus of claim 7 where the data processor generates Doppler frequency shift ($f_n$) and standard deviation $\sigma_n$ values at the nth pixel with complex analytical signals from the four sequential A-scans.

9. The apparatus of claim 8 where the data processor generates an average of the Doppler frequency shift ($f_n$) and standard deviation $\sigma_n$ values at the nth pixel for each polarization state to generate tomographic Doppler shift and variance images.

10. The apparatus of claim 1 where the sensor detects two orthogonal polarization diversity channels, and where the data processor generates the coherence matrix therefrom to generate the Stokes vectors characterizing the polarization state of the backscattered light, and the light intensity.

11. The apparatus of claim 10 where the data processor generates the Stokes vectors according to:

$$S_{0,n} = \sum_{m=n-M/2}^{n+M/2} \sum_{j=1}^{4} \left[ \Gamma_j^H(t_m)\Gamma_j^{H^*}(t_m) + \Gamma_j^V(t_m)\Gamma_j^{V^*}(t_m) \right]$$

$$S_{1,n} = \sum_{m=n-M/2}^{n+M/2} \sum_{j=1}^{4} \left[ \Gamma_j^H(t_m)\Gamma_j^{H^*}(t_m) - \Gamma_j^V(t_m)\Gamma_j^{V^*}(t_m) \right]$$

$$S_{2,n} = \sum_{m=n-M/2}^{n+M/2} \sum_{j=1}^{4} 2\mathrm{Re}\left[ \Gamma_j^{H^*}(t_m)\Gamma_j^V(t_m) \right]$$

-continued $$S_{3,n} = \sum_{m=n-M/2}^{n+M/2} \sum_{j=1}^{4} 2\mathrm{Im}\left[ \Gamma_j^{H^*}(t_m) \right]$$

where $\Gamma_j^H(t_m)$ and $\Gamma_j^V(t_m)$ are the complex signals detected from the two orthogonal polarization channels at axial rime $t_m$ for the jth A-scan, $\Gamma_j^{H^*}(t_m)$ and $\Gamma_j^{V^*}(t_m)$ are their conjugates.

12. The apparatus of claim 1 where the data processor generates the structural image from averaging the Stokes vectors for the four states of light polarization.

13. The apparatus of claim 1 where the data processor generates the phase retardation image from $S_0$, which characterizes the birefringence distribution in the sample by the rotation of the Stokes vectors in the Poincare sphere.

14. The apparatus of claim 1 where the polarization modulator provides light having selected Stokes vectors and where the sensor senses the elements of the Mueller matrix which are computed in the data processor.

15. The apparatus of claim 14 where the polarization modulator provides light having pure states of each of the selected Stokes vectors so that the Mueller matrix is directly measured.

16. A method of performing phase-resolved F-OCT to simultaneous image the Stokes vectors, structural, Doppler frequency shift, standard deviation, and birefringence of a sample comprising:
scanning the sample;
performing PS-OCT while scanning each pixel location;
simultaneously performing ODT while scanning each pixel location;
determining the Stokes vectors at each pixel location; and
generating the tomographic structural, Doppler frequency shift, standard deviation, and birefringence images of the sample.

17. The method of claim 16 further comprising averaging in the generation of the Doppler frequency shift and standard deviation to reduce the influence of speckle noise and tissue birefringence artifacts.

18. A method for performing phase-resolved functional optical coherence tomography of a sample characterized by optical birefringence comprising:
providing at least partially coherent polarized light in the source arm of an interferometer, the partially coherent polarized light being characterized by a well defined polarization state;
polarization modulating the light in a plurality of linearly independent polarization states;
phase modulating the light to generate a modulated optical path length difference in the reference and sample arms of the interferometer at a predetermined phase modulation frequency;
scanning the sample with the polarization and phase modulated light;
returning the polarization and phase modulated light to a detector arm in the interferometer from a reference arm in the interferometer,
returning the polarization and phase modulated light to a detector arm in the interferometer from a sample arm in the interferometer, where arbitrarily polarized and phase shifted light is returned to the detector arm from the sample arm according to sample birefringence and Doppler reflections from flowing fluid in the sample;
interfering the returned light from the reference arm and sample arm in the detector arm to form polarization and phase interference fringes;

detecting the polarization and phase interference fringes from the backscattered radiation; and processing the detected signals from the sensor corresponding to the interference fringes established by the backscattered radiation in the interferometer and to generate a complete polarization state description of the backscattered light from the sample by preserving phase relationships between orthogonal components of the polarization interference fringes formed from backscattered light from the sample and from the reference arm, and wherein the data processor simultaneously generates the Stokes vectors, and generates tomographic structure, blood flow velocity, standard deviation, and birefringence images at each pixel in the image.

19. The method of claim 18 where processing the detected signals processes data from A-line scans of the sample in each of the polarization states of the light impinging on the sample, and generates the tomographic blood flow velocity and standard deviation images by comparing the phase from pairs of analytical signals in the neighboring A-lines in the same polarization state.

20. The method of claim 18 where detecting the polarization and phase interference fringes detects two polarization diversity detection channels and where processing the detected signals generates the tomographic Stokes vector images by processing the analytical signals from the two polarization diversity detection channels for the same reference polarization state.

21. The method of claim 20 where generating the four Stokes vectors generates the tomographic birefringence image.

22. The method of claim 18 where polarization modulating the light modulates the polarization state of light in the sample arm, which rapidly varies between states orthogonal in the Poincare sphere at a predetermined frequency to insure that birefringence measurements are independent of orientations of the optical axis of the sample.

23. The method of claim 18 where detecting the polarization and phase interference fringes detects four states of light polarization at each pixel.

24. The method of claim 23 where scanning the sample comprises sequentially scanning a predetermined number of lateral line scans, A-line scans, for each polarization state.

25. The method of claim 24 where processing the detected signals generates Doppler frequency shift ($f_n$) and standard deviation $\sigma_n$ values at the nth pixel with complex analytical signals from the four sequential A-scans.

26. The method of claim 25 where processing the detected signals generates an average of the Doppler frequency shift ($f_n$) and standard deviation $\sigma_n$ values at the nth pixel for each polarization state to generate tomographic Doppler shift and variance images.

27. The method of claim 18 where detecting the polarization and phase interference fringes detects two orthogonal polarization diversity channels, and where processing the detected signals generates the coherence matrix therefrom to generate the Stokes vectors characterizing the polarization state of the backscattered light, and the light intensity.

28. The method of claim 27 where processing the detected signals generates the Stokes vectors according to:

$$S_{0,n} = \sum_{m=n-M/2}^{n+M/2} \sum_{j=1}^{4} \left[ \tilde{\Gamma}_j^H(t_m)\tilde{\Gamma}_j^{H^*}(t_m) + \tilde{\Gamma}_j^V(t_m)\tilde{\Gamma}_j^{V^*}(t_m) \right]$$

$$S_{1,n} = \sum_{m=n-M/2}^{n+M/2} \sum_{j=1}^{4} \left[ \tilde{\Gamma}_j^H(t_m)\tilde{\Gamma}_j^{H^*}(t_m) - \tilde{\Gamma}_j^V(t_m)\tilde{\Gamma}_j^{V^*}(t_m) \right]$$

$$S_{2,n} = \sum_{m=n-M/2}^{n+M/2} \sum_{j=1}^{4} 2\text{Re}\left[ \tilde{\Gamma}_j^{H^*}(t_m)\tilde{\Gamma}_j^V(t_m) \right]$$

$$S_{3,n} = \sum_{m=n-M/2}^{n+M/2} \sum_{j=1}^{4} 2\text{Im}\left[ \tilde{\Gamma}_j^{H^*}(t_m) \right]$$

where $\Gamma_j^H(t_m)$ and $\Gamma_j^V(t_m)$ are the complex signals detected from the two orthogonal polarization channels at axial rime $t_m$ for the jth A-scan, $\Gamma_j^{H^*}(t_m)$ and $\Gamma_j^{V^*}(t_m)$ are their conjugates.

29. The method of claim 18 where processing the detected signals generates the structural image from averaging the Stokes vectors for the four states of light polarization.

30. The method of claim 18 where processing the detected signals generates the phase retardation image from $S_0$, which characterizes the birefringence distribution in the sample by the rotation of the Stokes vectors in the Poincare sphere.

31. The method of claim 18 where polarization modulating the light comprises modulating the light to assume a characterization selected Stokes vectors and where the processing the detected signals generates the elements of the Mueller matrix.

32. The apparatus of claim 31 where modulating the light to assume a characterization selected Stokes vectors provides light having pure states of each of the selected Stokes vectors so that the Mueller matrix is directly measured.

* * * * *